United States Patent [19]
Schug

[11] Patent Number: 5,571,185
[45] Date of Patent: Nov. 5, 1996

[54] PROCESS FOR THE PRODUCTION OF A BONE IMPLANT AND A BONE IMPLANT PRODUCED THEREBY

[75] Inventor: Martin Schug, Lübeck, Germany

[73] Assignee: ESKA Implants GmbH, Lubeck, Germany

[21] Appl. No.: 75,494

[22] PCT Filed: Oct. 10, 1992

[86] PCT No.: PCT/EP92/02335

§ 371 Date: Sep. 30, 1993

§ 102(e) Date: Sep. 30, 1993

[87] PCT Pub. No.: WO93/07835

PCT Pub. Date: Apr. 29, 1993

[30] Foreign Application Priority Data

Oct. 12, 1991 [DE] Germany .................. 41 33 877.4

[51] Int. Cl.⁶ ................................................ A61F 2/28
[52] U.S. Cl. .................................................. 623/16
[58] Field of Search ..................... 623/16; 433/173, 433/176, 201, 220, 221

[56] References Cited

U.S. PATENT DOCUMENTS 4,492,577  1/1985  Farris et al. ................. 433/201
5,042,560  8/1991  Ahlers ........................ 164/34

Primary Examiner—Randy C. Shay
Attorney, Agent, or Firm—Panitch Schwarze Jacobs & Nadel, P.C.

[57] ABSTRACT

A process is disclosed for producing a bone implant which has at least in sections a surface structure with open pores. The positive model for the implant is moulded from a base body made of a modelling material coated at least in sections with a porous coating having a predetermined pore structure. Also disclosed is a bone implant made of metal or plastics with a local distribution of pore sizes and/or densities at the surface of the implant that corresponds to the trabecular structure of the osseous environment in which the implant is implanted.

12 Claims, 11 Drawing Sheets

PROCESS FOR THE PRODUCTION OF A BONE IMPLANT AND A BONE IMPLANT PRODUCED THEREBY

Description

The invention relates to a process for the production of a bone implant made from metal or plastic, in which a positive moulding is produced from a member of moulding material, which at least in sections possesses an open-pore or open-cell structure on the surface comprising a predetermined porous structure made from moulding material, the positive moulding is embedded into a ceramic embedding compound filling the pores of the open-pore structure to form a core, the moulding material is removed by the use of heat which produces, spaces in the remaining core, which spaces were previously occupied by the moulding material the spaces are filled by casting or centrifuging with the metal or plastic, and subsequently the core material is removed to form the implant.

The invention also relates to a bone implant.

A process is known for example from German Patent Specification 31 06 917 or from German Patent Specification 32 24 265, in which an open-pore plastic moulding member, for example an open-pore or open-cell natural or synthetic sponge, is used as the positive moulding. The open-pore surface of the positive moulding results in the production of an implant having an open-pore surface structure, whereby the open pores of the cells in each case should be the same size or larger than the spongy trabeculae of a natural bone, so that the ingrowth of the osseous tissue with subsequent bone formation begins immediately after implantation. However as the pore size occurs statistically distributed within predetermined limits in the plastic member used as the positive cast, and as the pores are also at random, an implant surface is produced in which the pores are locally distributed at random. The ingrowth of spongiosa trabeculae, which in the adjacent osseous tissue possess a naturally ordered structure, is impeded by the arbitrary distribution of the pores on the implant surface.

The object of the invention is therefore to provide a process for the production of a bone implant possessing an open-pore surface structure covering comprising a predetermined pore structure.

A further object of the invention is also to provide a bone implant having an open-pore surface structure which facilitates the ingrowth of the adjacent osseous tissue in comparison to known structures.

The object is achieved in accordance with the invention by an implant which made of metal or plastic, processing an open-pore surface structure and which is characterised in that the pore size and/or pore density on the surface of the implant has a local distribution which corresponds to the trabecula structure of the bone environment in which the implant is attached.

The advantages of the invention lie particularly in the fact that implants having an open-pore surface structure can be produced which, with respect to their local distribution of the pore size and density, correspond to the spongiosa trabecula structures present at the implant site to an extent hitherto not achieved. This adaption of the pore distribution with respect to size, density and depth is possible according to the invention on the surface of an implant and allows the pore and cell sizes to be adapted to the spongiosa trabecula structure of the surrounding osseous tissue so that many spongiosa trabeculae also encounter a correspondingly large number of pores arranged according to the natural conditions. As the distribution of the spongiosa trabeculae in the bone are ordered with respect to their size, density and with respect to their local position, a corresponding arrangement of the surface pores of the implant produced in accordance with the invention can improve the anchoring quality.

In the process according to the invention the local distribution of the pore size and/or pore density of the structural covering applied to the positive moulding is reproduced on the surface of the bone implant produced. Therefore a distribution of the pore sizes and/or density is particularly preferably chosen so that this distribution roughly corresponds to the structure of the spongy tissue, which is present in the vicinity in which the implant is to be placed.

According to a particularly preferred embodiment of the invention, the structural covering has a regular, uniform structure consisting of threads and/or webs and spaces located therebetween, which form the pores. A knitted, woven or braided fabric, which has a periodic structure, the periodicity of which can constantly change as a function of the site, is preferably used as the structural covering. The alteration in this periodicity of the structural covering can either be achieved by a local alteration of the threads or webs forming the structural covering, or alternatively this alteration can be also achieved by a locally variable elongation or extension of a per se uniform structural covering.

In a particularly preferred manner, the pore depth and/or the thickness of the structural covering on the base member alters in a locally predetermined manner. A particularly preferred local distribution of the pores of the structural covering on the base member corresponds to the trabecula structure of the bone bed, into which the implant is to be subsequently inserted. In this way a fine structure of the open pores on the implant surface is achieved, which enables a particularly fast and adapted ingrowth of the adjacent spongy tissue into the pores, and as a result a particularly secure fit between the bone and implant.

If, for example, a thigh part of a hip joint prosthesis is used as the implant, according to the invention the structural covering or respectively the knitted/woven or braided fabric can be applied to the positive moulding in such a manner that the webs or threads, and therefore the pores, are disposed on the positive moulding in curves, which correspond to the trajectories of the spongy tissue present in the upper femur, so that the spongiosa trabeculae, which are disposed along these trajectories, can grow into the pores of the implant according to their natural growth inclination.

In accordance with the invention the pore size and/or pore depth—in a thigh part to be used - on the positive moulding is particularly preferably specified so that the pore size and/or depth decreases towards the distal end of the prosthesis shaft and in the proximal shaft region corresponds to the relatively large spongiosa trabeculae there. Alternatively only a proximal section of the base member is provided with structural covering, but the adjacent distal section on the other hand is free from structural material so as to produce a smooth surface.

A base member made of wax or a heat-volatile plastic is preferably produced as the positive cast, whereby the base member can be made from solid material or also from an open-pore material. Subsequently the knitted, braided or woven fabric made from plastic material is applied, which evaporates with the action of heat and is therefore suitable as the moulding material and which has the desired pore distribution. If necessary, the positive moulding may be immersed in liquified wax or a wax-water emulsion or be sprayed with wax or a wax-water emulsion before being embedded in the embedding ceramic in order to bring the webs of the knitted or braided fabric located between the pores to a desired thickness. When embedding the positive moulding in the ceramic embedding compound, the pores are filled with embedding compound and then the core is compacted by the action of heat, as a result of which the moulding material evaporates. With the subsequent pouring in of metal the negatively imitated pores—now in the core material—remain free from metal. If the core material is subsequently removed, for example by acid solutions, such as for example hydrofluoric acid, an implant made of metal is produced, which on its surface possesses the pore structure originally produced on the positive cast.

According to a particularly preferred embodiment of the invention, the knitted, woven or braided fabric contains longitudinal webs, which intersect the longitudinal webs at predetermined angles, because with such a web structure the trabecula structure of the natural flat tissue can be imitated particularly well.

If a femur prosthesis is to be produced, then the positive moulding has a corresponding oblong shaft. In accordance with the invention the knitted, woven or braided fabric made of moulding material is applied to the base member of the positive moulding in such a manner that the longitudinal and transverse webs extend in preferred directions on the base member. The longitudinal webs posses a distinctive directional component in the longitudinal direction of the shaft, and the transverse webs have a corresponding directional component in the circumferential direction.

The longitudinal webs and the transverse webs are preferably formed by an accumulation and/or a thickening of threads extending in the web direction.

The knitted, woven or braided fabric can be placed as a mat on the base member of the positive moulding and be attached there. Alternatively the knitted, woven or braided fabric can be constructed as a hose, which is pulled on the base member. If the knitted, woven or braided fabric is made from elastic moulding material, then when the hose is pulled on to the base member an automatic expansion and adjustment of the shape of the tissue structure occurs, which, with the greater expansion of the tissue, for example at the proximal section of the shaft of a femur prosthesis, results in an enlargement of the pores or cells.

The longitudinal threads and transverse threads of the knitted, woven or braided fabric are particularly preferably constructed in one layer. However alternatively multi-layer knitted or woven fabrics are possible, which result in a complexity of the pore formation and in an enlargement of the pore depth. The longitudinal threads and/or transverse threads may be wave-shaped within their layer and be connected to one another by means of loops or by gluing or bonding.

In accordance with the invention the open-pore structure is achieved in that on the surface of the implant is tip-stretched a uniform hollow lattice structure, which consists of wire-shaped lattice webs or filaments and between and beneath the lattice webs produces spaces which form pores which are open to the outside. In order to structure the pores, i.e. the spaces between and beneath the lattice webs, in the desired manner corresponding to the trabecula structure of the bone environment, the lattice webs along the trajectories of the spongy tissue must correspond to the natural bone adjacent implant site. Woven, knitted or braided structures, the filaments of which are formed as wire-shaped lattice webs, are suitable as the hollow lattice structure.

The hollow lattice structure on the surface of the implant is particularly preferably integrally tip-stretched from implant material. Alternatively the hollow lattice structure may however be produced as a separate covering from the implant material, which is welded onto a base member of the implant or connected in another suitable way.

The hollow lattice structure on the surface of the implant can be disposed in locally variable lattice depths from single-layer or multi-layer lattice webs.

In order to produce a porous structure in which an adequate positive locking is achieved between the implant and the ingrowing spongiosa material, at least some of the wire-shaped lattice webs preferably extend in waves on the implant core and are only connected by predetermined longitudinal sections with the implant core, while the transverse webs extend over the intermediate sections at a distance from the solid implant core. The lattice webs are then surrounded on all sides by the spongy tissue growing back in intermediate sections spaced from the implant core.

Advantageous refinements of the invention are characterised by the features of the subordinate claims.

Exemplified embodiments of the invention are explained in further detail below by means of the drawings.

Figure 1:
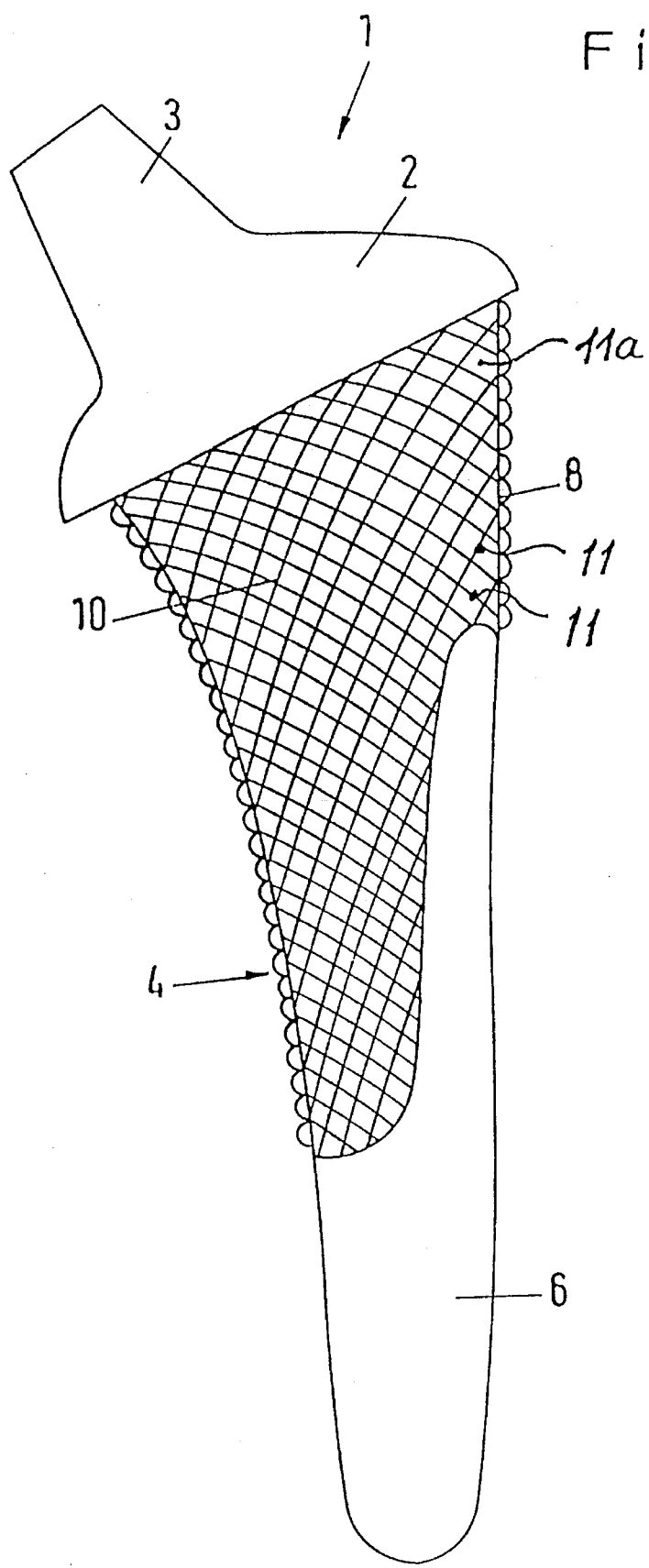
FIG. 1 shows a thigh part of a hip joint endoprosthesis produced by the process in accordance with the invention.

FIG. 1 shows, as a special case of a bone implant, the thigh part of a hip joint endoprosthesis. A shaft 4 has a distal section 6, which comprises a closed or smooth surface, and a proximal section 8, which supports an open-pore structure on the surface. The proximal section 8 ends at the collar 2, which is adjacent to a conical neck section 3, onto which a prosthetic articulated spherical part can be placed.

The proximal section 8 of the implant is provided with an open-pore or open-cell surface structure. To produce the open-pore or open-cell surface structure, a uniform hollow lattice structure made from implant material is integrally tip-stretched on the solid shaft core. The hollow lattice structure 10 consists of wire-shaped lattice webs 11, which are orientated in predetermined directions on the implant core. Between and beneath the lattice webs 11 lie spaces 11*a*, which form the pores open to the outside. As can be seen from FIG. 1, the pore size or pore density of the surface structure 10 in the proximal section is locally structured so that the pores have a distribution which corresponds to the trabecula structure of the spongiosa tissue of the femur, in which the implant is anchored, cf. FIGS. 14 to 17.

FIG. 2 to 6 show a positive moulding for a thigh part of a hip joint endoprosthesis in lateral elevation and in different detailed elevations. The positive moulding 12 possesses a shaft 16 having a distal free end 17. At the proximal end the shaft 16 is surrounded by a collar having a conical neck projection 14. Alternatively the neck may be provided in one piece with a spherical prosthesis head.

The positive moulding 12 is composed of a single-piece base member 15 made from wax or a heat-volatile plastic comprising a shaft core having a tip-stretched neck projection 14. The shaft core—in the embodiment shown is covered with a porous structural covering, for example a knitted, woven or braided material 18 made from heat-volatile moulding material, for example an elastic plastic material and on the shaft core produces a predetermined porous structure. The knitted, woven or braided fabric 18 is, for example, prefabricated as a homogenous expandable hose having a constant structure over the entire length and is then applied to the shaft core. As the hose made from moulding material at the widening of the shaft core which increases to the neck projection 14 stretches in a corresponding manner, in the upper region of the shaft larger spaces are produced between the threads or webs 24, 26 and as a result a porous structure is produced which has been stretched more and has larger pores than at the distal shaft end 17.

Figure 2:
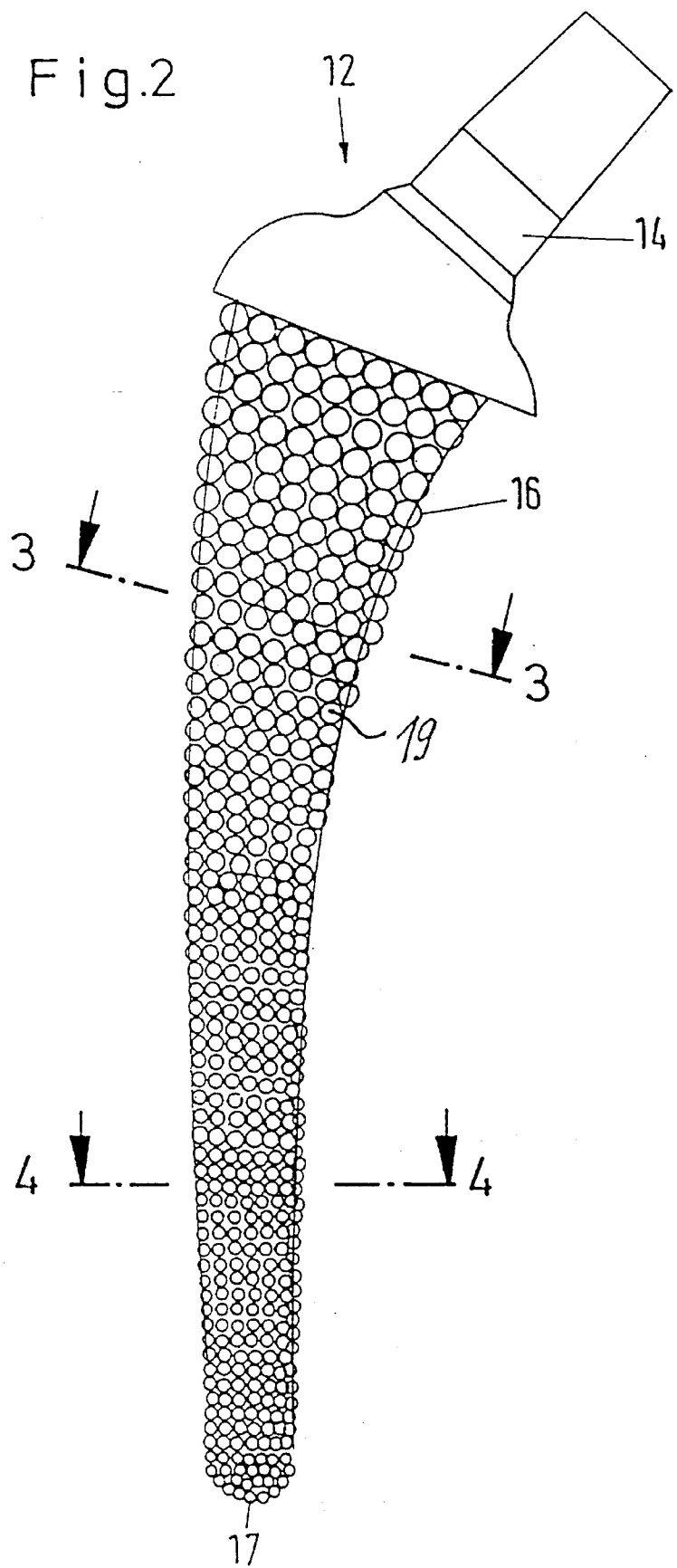
FIG. 2 shows a positive moulding for a thigh part of a hip joint endoprosthesis.
Figure 3:
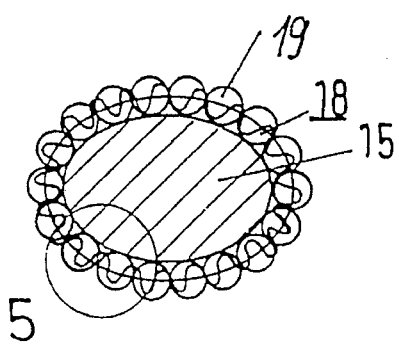
FIG. 3 shows a cross section along line A—A of FIG. 2.
Figure 4:
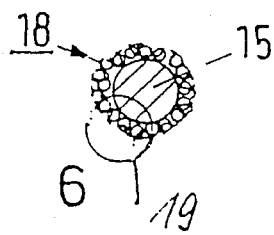
FIG. 4 shows a cross section along line B—B of FIG. 2.
Figure 5:
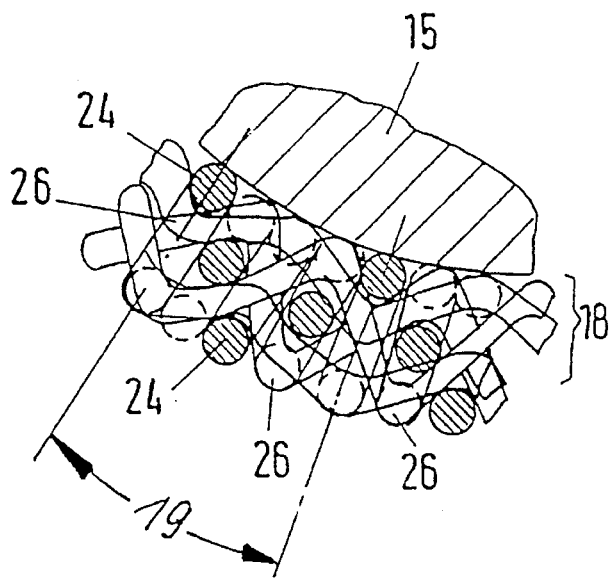
FIG. 5 shows a detailed view X from FIG. 3.
Figure 6:
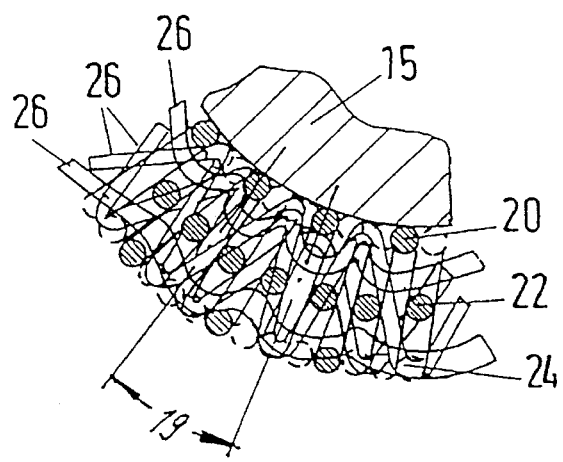
FIG. 6 shows a detailed view Y from FIG. 4.

The structural covering 18 applied to the shaft core as shown in FIG. 2 is constructed in several layers, it consists of a three-layer woven or braided fabric having longitudinal threads 24 of the different layers, cf. FIG. 3 to 6. The circles represented in FIG. 2 and 3 mark a basic period or a basic cell having a predetermined thread structure, to which the next basic period or basic cell is attached on all sides, in which the thread structure of the basic cell is identically repeated. As can be seen in FIG. 2 to 4, the basic period is at its largest in the proximal region of the shaft 16 and gradually and constantly decreases towards the distal shaft end 17. In FIG. 5 and 6, which are detailed representations X and Y respectively of FIG. 3 and 4, is represented a cross-section through a basic cell 19 of the structural covering 18.

Figure 7:
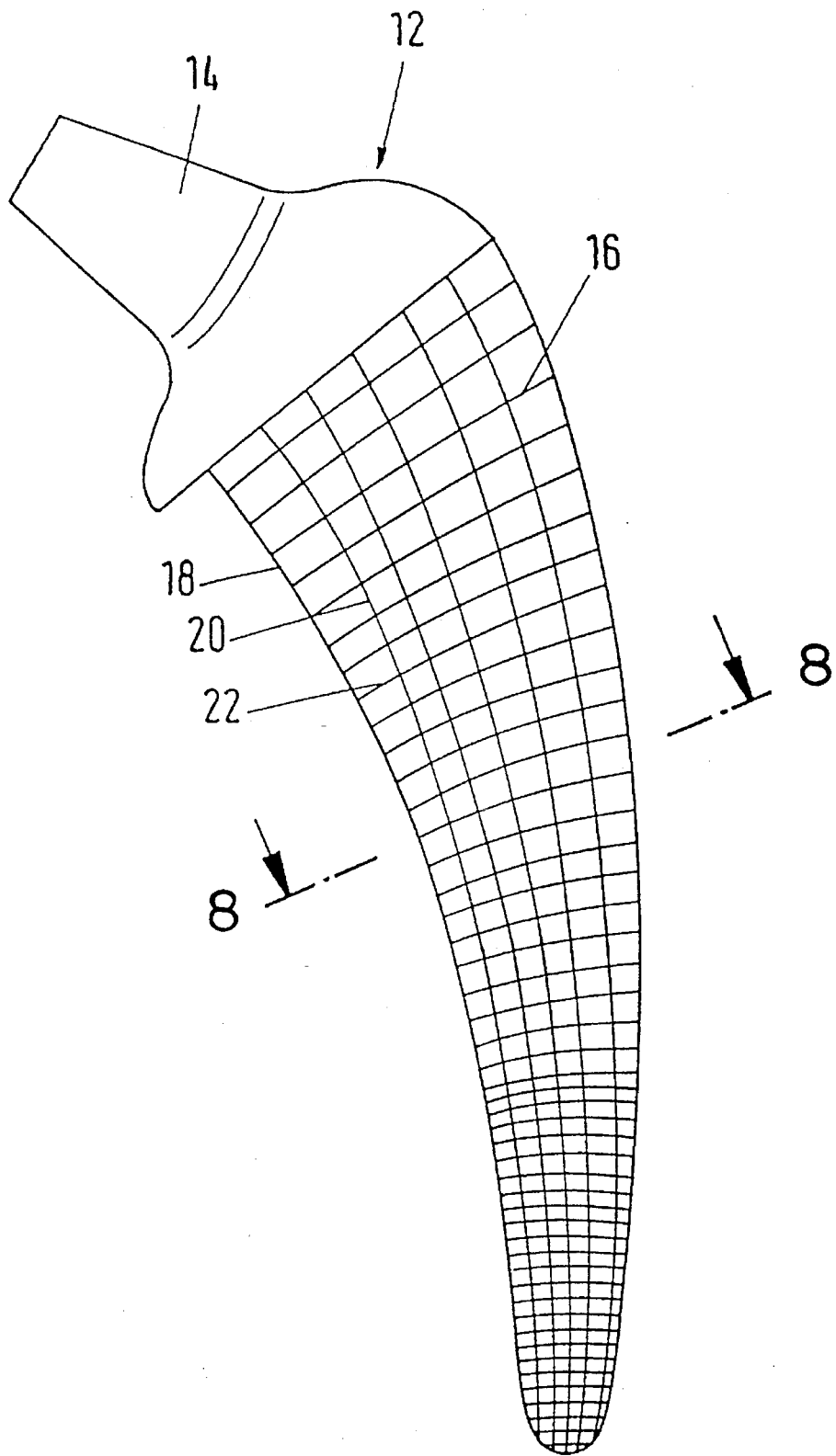
FIG. 7 shows a further positive moulding of a thigh part of a hip joint endoprosthesis.
Figure 8:
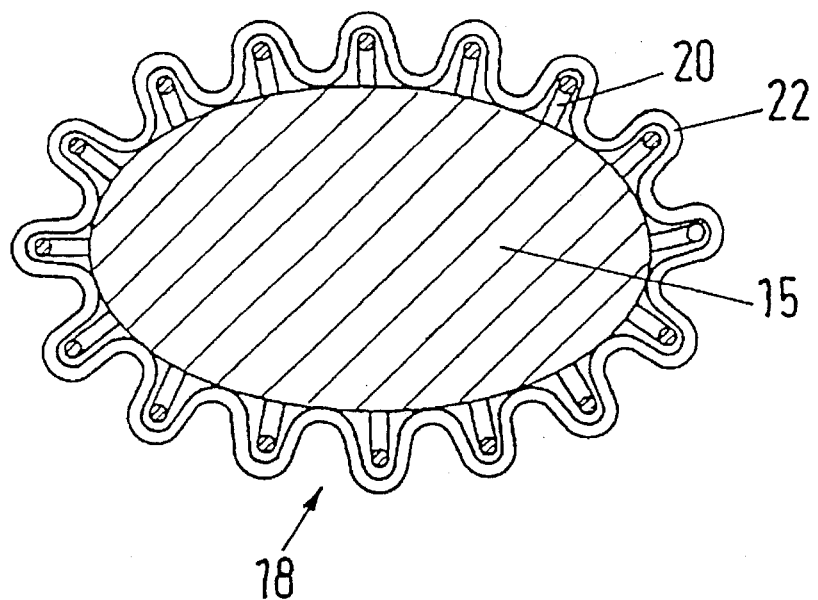
FIG. 8 shows a cross section along line A—A from FIG. 7
Figure 9:
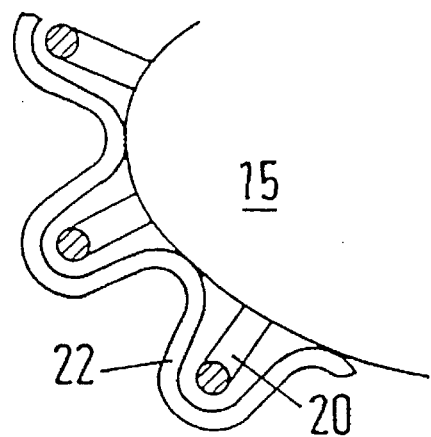
FIG. 9 shows a detail from FIG. 8.

FIG. 7 to 9 show a further positive moulding for a thigh part of a hip joint endoprosthesis in a further embodiment. The base member 15 made from moulding material itself consists of a shaft core 15 with neck projection 14 tip-stretched at the proximal end. To produce the desired porous structure, the shaft core is covered with a knitted, woven or braided fabric 18 made from moulding material, for example heat-volatile plastic. The structure of the coating 18 is selected so that longitudinal webs 20 and transverse webs 22 crossing the longitudinal webs 20 and transverse webs 22 intersect almost at right angles, the longitudinal webs 20 extend in the shaft direction, and the transverse webs 22 extend in the circumferential direction of the shaft 16. As can be seen in particular from FIG. 8 and 9, the longitudinal webs are produced from individual, spaced, undulating longitudinal threads, and the transverse webs 22 are formed from correspondingly spaced transverse threads 26, which connect the longitudinal threads 24 to one another in a wave shape.

Figure 10:
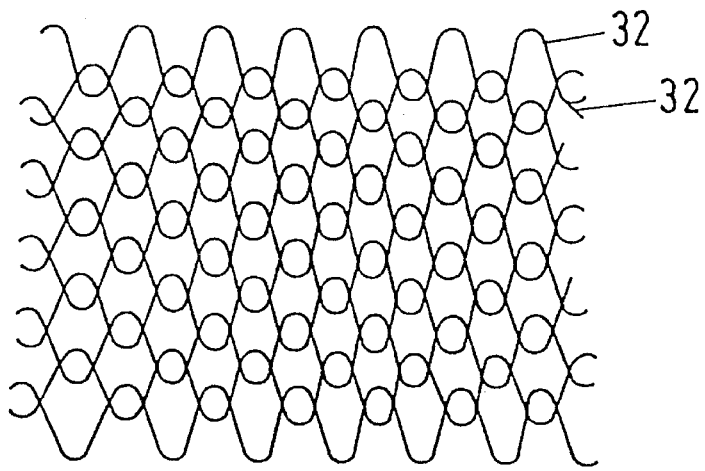
FIG. 10 shows a plan view of the structure of a knitted fabric, which is suitable for covering a base member.
Figure 11:
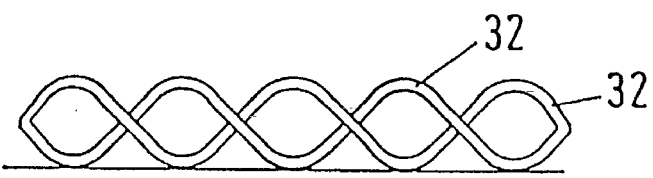
FIG. 11 shows a cross section along line A—A through FIG. 10.

FIG. 10 and 11 show a plan view of a knitted fabric 18, which is also suitable for covering a base member 15. Transverse threads 32 are shown, which are meshed and cross-linked to one another.

Figure 12:
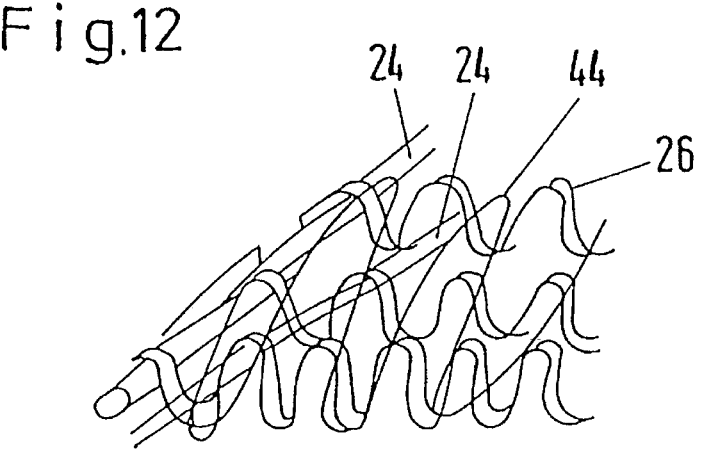
FIG. 12 shows a plan view of a further knitted structure.

In FIG. 12 is represented a further knitted structure 18, in which spaced longitudinal threads 24 are connected to undulating transverse threads 26. To improve the strength of the woven, braided or knitted fabric are also provided mesh threads 44 extending in the longitudinal direction.

Figure 13:
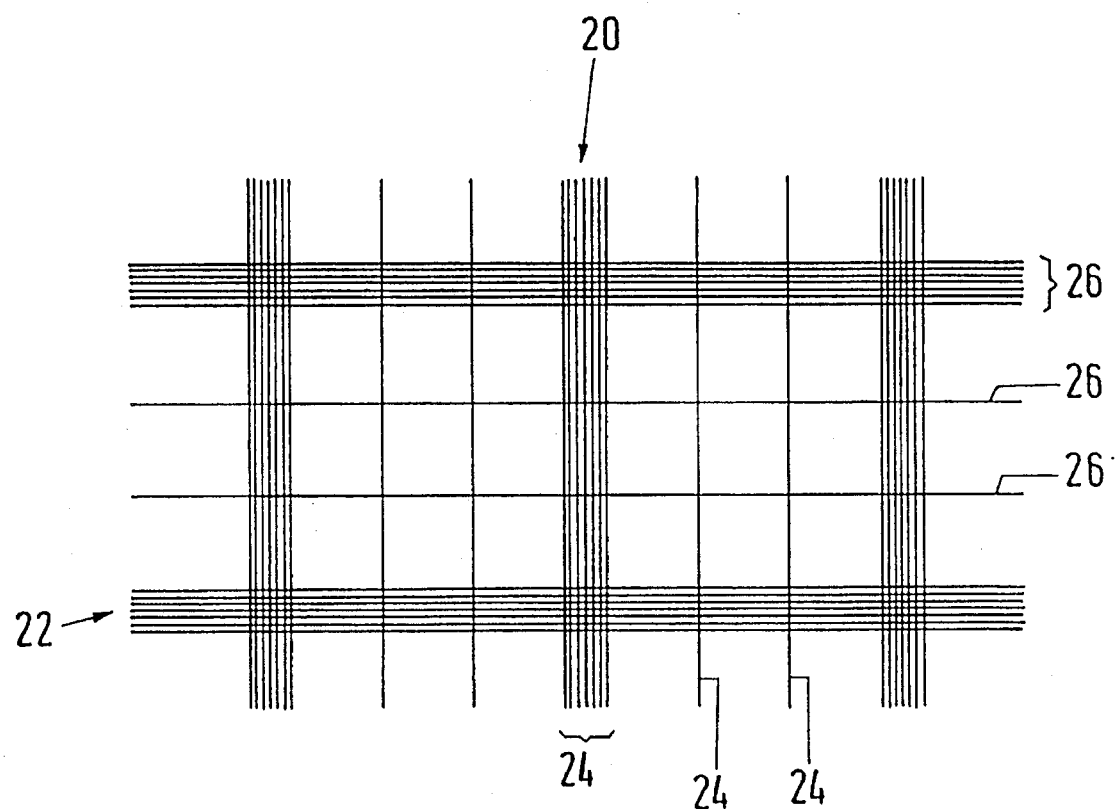
FIG. 13 shows a further plan view of a woven or braided structure.

FIG. 13 shows an enlarged plan view of a knitted, braided or woven fabric 18, in which longitudinal webs 20 and transverse webs 22 intersect at right angles to one another, whereby the webs 20, 22 are formed by an accumulation of threads 24, 26. Longitudinal threads and transverse threads can be bonded to one another at the intersection points or can be connected in another suitable manner, for example by cross-linking.

Figure 14:
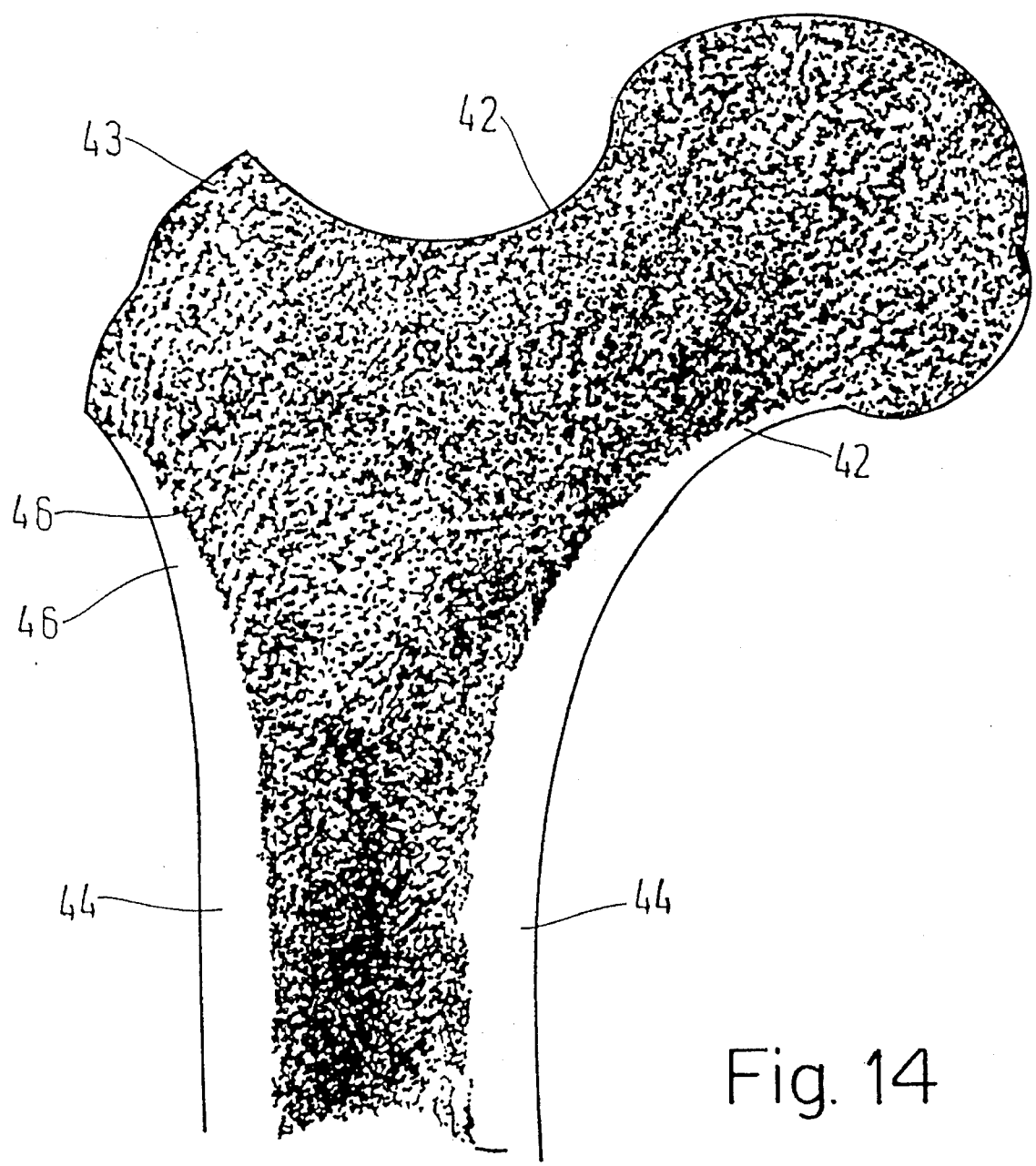
FIG. 14 shows a section through the upper region of a femur bone.
Figure 15:
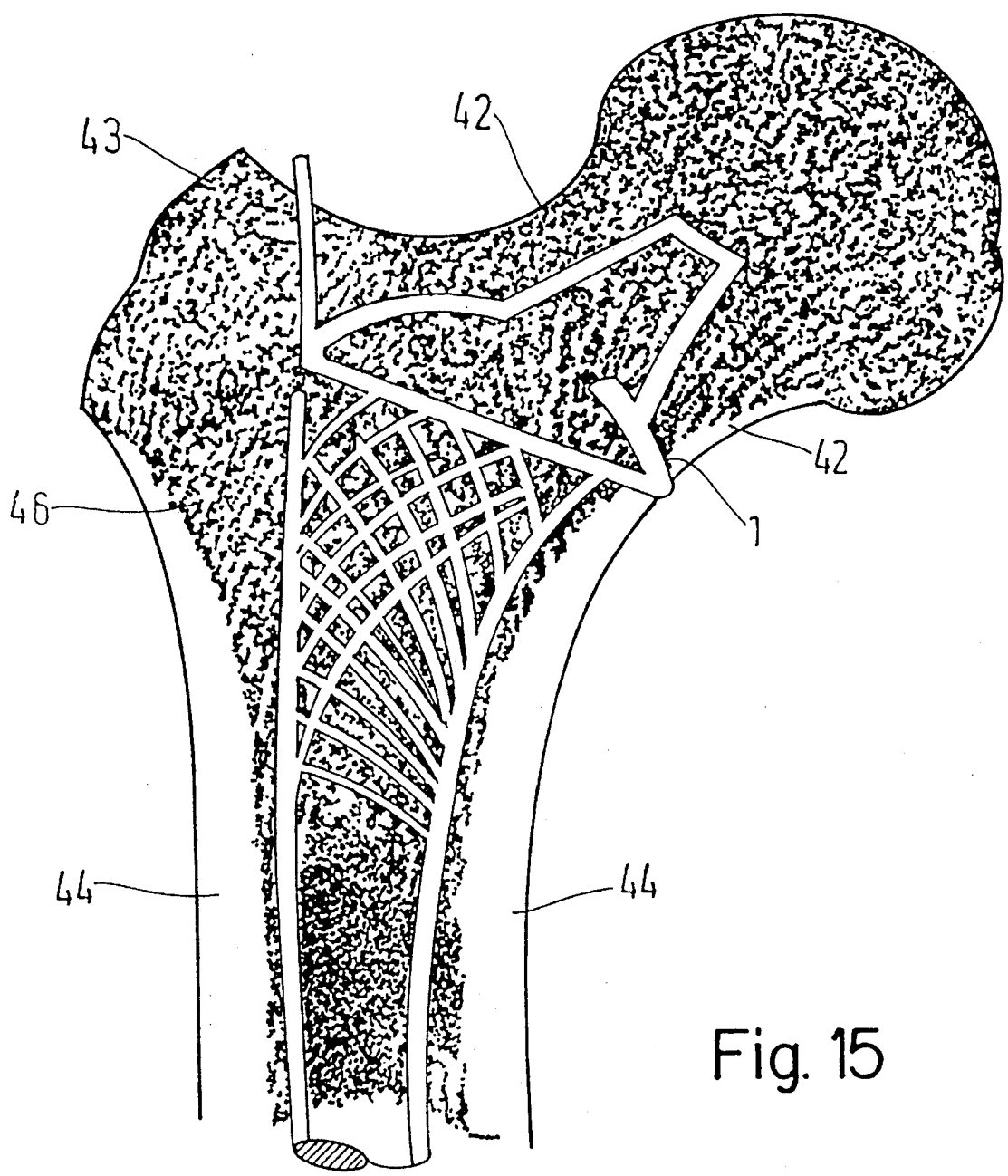
FIG. 15 shows a section as in FIG. 14 but with a hip joint prosthesis according to the invention.

FIG. 14 and 15 represent a cross section through the upper region of a femur bone without or with an inserted hip shaft prosthesis. The trabecula structure of the spongy tissue is clearly visible. The trajectories 46 of the spongy tissue start at the cortical substance 44 of the bone and extend upwards curved substantially in a circle either into the neck region 42 or the region of the greater trochanter 42. An implanted hip shaft endoprosthesis 1 is diagrammatically shown, which beneath its collar 2 in its proximal shaft section comprises an open-pore surface structure in the form of a hollow lattice structure 100. The hollow lattice structure 100 is formed by wire-shaped lattice webs, which between and beneath them produce spaces which form the pores of the structure which are open to the outside. As can be clearly seen in FIG. 14 and 15, the wire-shaped lattice webs of the prosthesis 1 extend along the trajectories 46 of the spongy tissue of the adjacent natural implant site.

Figure 16:
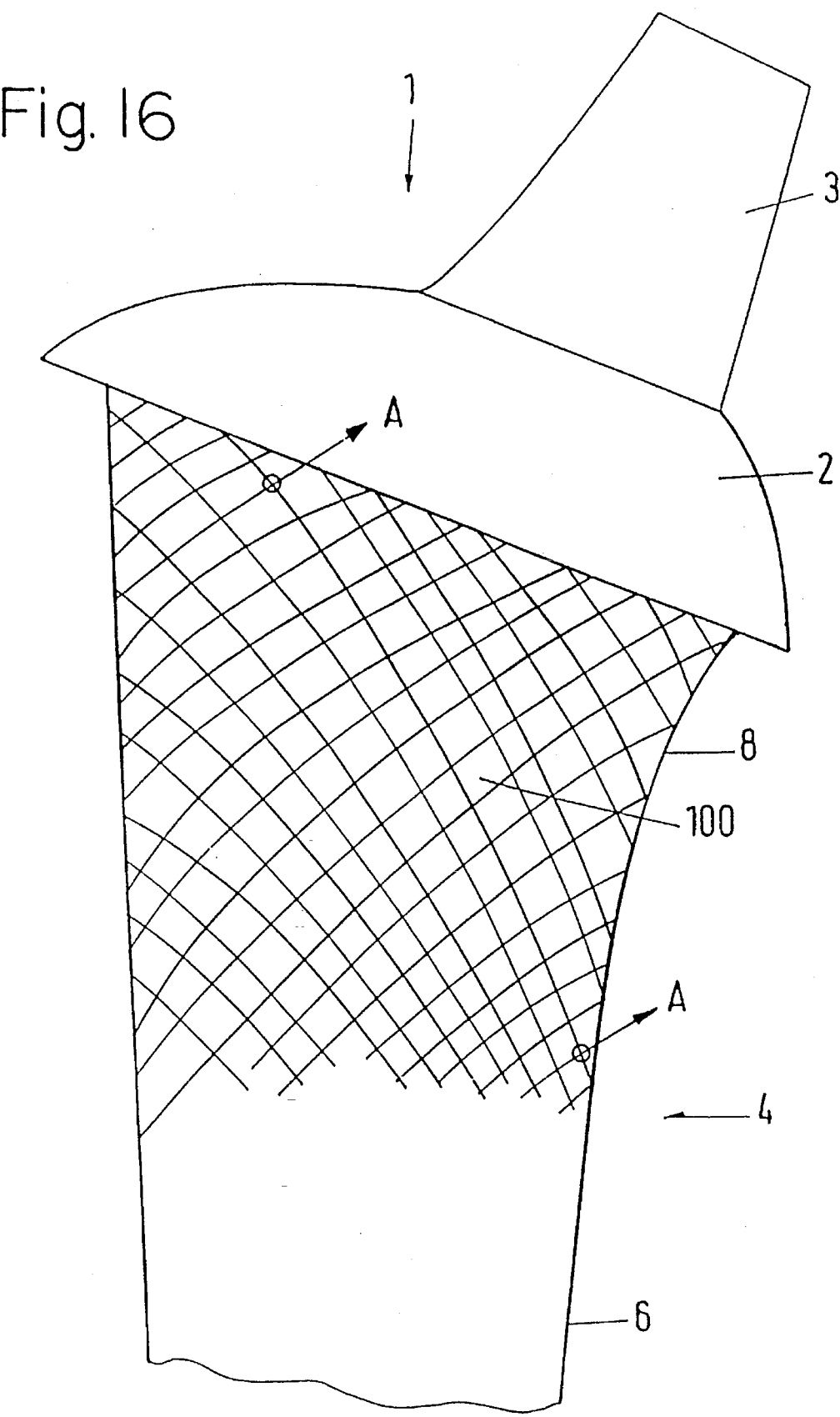
FIG. 16 shows a lateral elevation of the proximal region of a hip shaft prosthesis according to the invention.

FIG. 16 shows an enlarged lateral elevation of the hip shaft prosthesis 1 diagrammatically represented in FIG. 15, whereby the lower part of the prosthesis is broken away to enlarge the representation. The hip shaft prosthesis 1 diagrammatically represented in FIG. 15, whereby the lower part of the prosthesis is broken away to enlarge the representation. The hip shaft prosthesis 1 contains a shaft 4, at the proximal section 8 of which a collar 2 laterally protruding over the shaft with a conical neck section 3 is tip-stretched. The proximal section 8 of the shaft 4 passes—towards its free end—into a distal section 6, which is partially broken away. The proximal shaft section 8 possesses an open-pore surface structure, which is integrally tip-stretched at the shaft core as a hollow lattice structure 100 and consists of several intersecting, wire-shaped lattice webs 102 to 112, the height of the hollow lattice structure 100 continuously decreased towards the distal section 6, so that the distal section 6—in the exemplified embodiment represented—possesses a smooth, structure-free surface.

Figure 17:
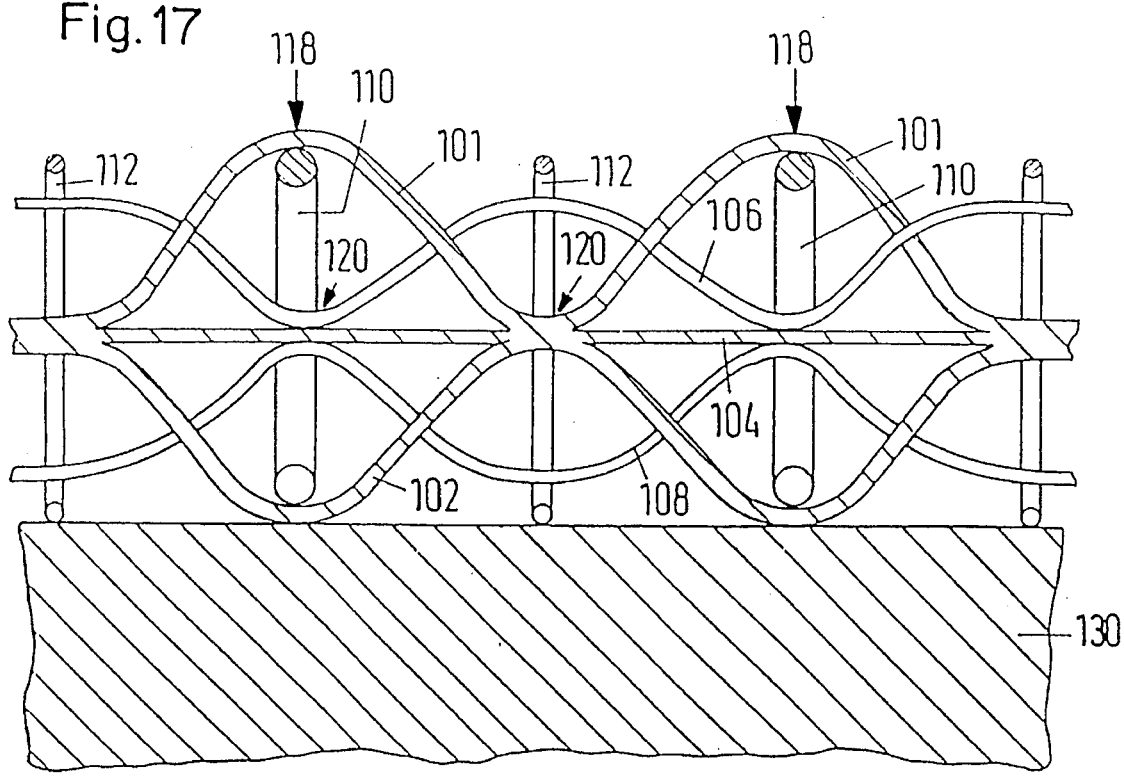
FIG. 17 shows a section along line A—A of FIG. 16.
Figure 18:
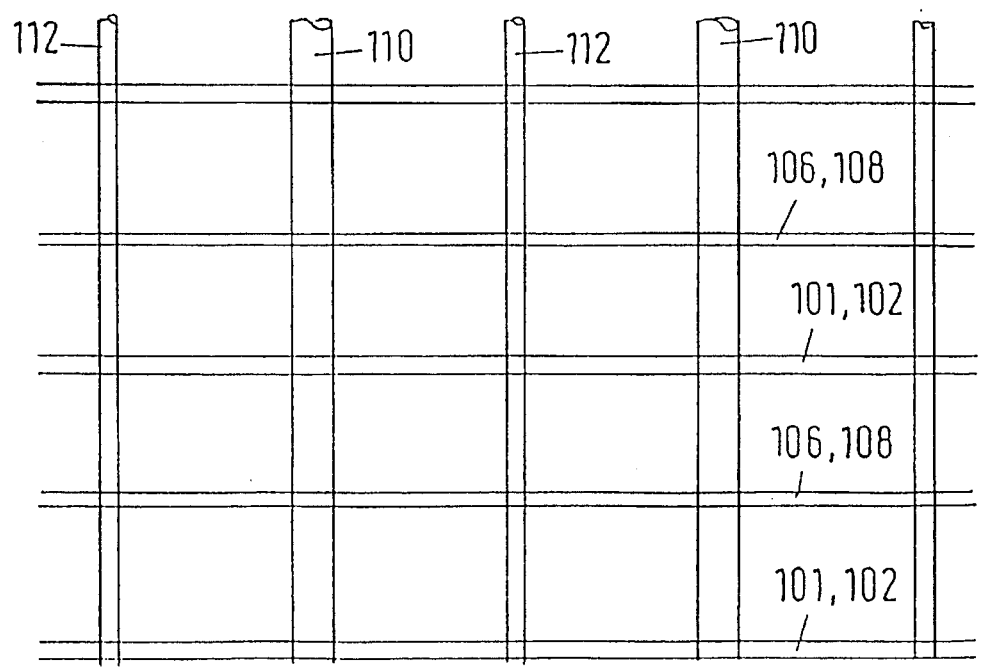
FIG. 18 shows a plan view of the structure shown in FIG. 17.

FIG. 17 represents a section along line A—A of FIG. 16 on an enlarged scale, and FIG. 18 is a plan view of the structure of FIG. 17.

The hollow lattice structure 100 is integrally tip-stretched on the implant core 130 made from metal or plastic. In the intersection plane extend two wire-shaped lattice webs 101, 102 as mirror images of one another and form loops 118 and burls 120, whereby the lattice web 102 close to the implant core is connected to the implant core 130 at the loops, and the lattice webs 101, 102 are connected to one another at the burls 120. In the embodiment represents a further rectilinear lattice web 104 extends through the burls in the intersection plane. Further lattice webs 101, 102 and 104, which have the same path as the lattice webs 101, 102 and 104, which are represented cut-off, and also the same, relatively thick cross section, extend—in the direction of the trajectories of the adjacent osseous tissue—at a predetermined distance, roughly parallel to the lattice webs 101, 102 and 104, which are represented but-off. Between the groups of lattice webs 101, 102 and 104 extend, roughly parallel to these lattice webs 101, 102 and 104, but with a smaller cross section, further groups of lattice webs 106, 108, the burls of which lie in the plane fixed by the burls 120, which however have a smaller amplitude than lattice webs 101 and 102 and therefore do not touch the implant core 130 in the loop sections. The loops and burls of the lattice webs 106, 108 are offset with respect to the loops and burls 118, 120 of the lattice webs 101 and 102 by half a wavelength.

At right angles to the lattice webs 101 to 108 extend—in the burls 118 of the lattice webs 101 and 102—further lattice webs 110 formed in waves, the amplitude of which is the same as the entire loop amplitude of the lattice webs 101 and 102. Over the loops of the lattice webs 106 and 108 also extend wave-shaped lattice webs 112 having a smaller cross section, the amplitude of which is roughly the loop amplitude of the lattice webs 101 and 102. Lattice webs 112 are integrally connected in predetermined sections to the implant core 130.

The lattice webs 101 to 108 extend over the implant core, as shown in FIG. 14 and 15, along the trajectories of the adjacent spongy tissue, i.e. from the ventral side curved roughly in circle upwards to the collar 2 or to the lateral boundary line of the shaft. The lattice webs 110, 112 also extend along the trajectories of the adjacent spongy tissue, beginning at the lateral boundary contours of the prosthesis curved roughly as a circle upwards to the collar 2 and to the ventral contours respectively.

Apart from the hollow lattice structure 100 shown, in accordance with the invention any modifications and variations in the hollow lattice structures are possible and are within the scope of the present disclosure.

I claim:

1. A process for the production of a bone implant made from metal or plastic and having at least a portion of a surface of the implant covered with an open-pore or open-cell structure, comprising the steps of:

(a) producing a base member for a positive molding of a bone implant from a molding material, (b) forming a porous structural covering from a molding material, said covering having an open-pore or open-cell structure;

(c) applying the covering of step (b) to at least a portion of a surface of the base member of step (a) to form the positive molding in such a manner that pores or cells of the structural covering are arranged on the base member in a local distribution which corresponds to a trabecular structure of a bone environment into which the implant is to be inserted, (d) embedding the positive molding into a ceramic embedding compound to fill the pores or cells with ceramic compound, (e) removing the molding material of the base member and covering by application of heat to form a ceramic core having spaces which were previously occupied by the molding material, (f) filling the spaces in the ceramic core by casting or centrifuging with metal or plastic, and (g) removing the ceramic core to form the implant.

2. The process according to claim 1, wherein the step of forming the porous structural covering comprises providing a regular structure of threads or webs with spaces therebetween which form the pores or cells.

3. The process according to claim 2, wherein the step of applying the covering to the base member comprises disposing the threads or webs of the covering along predetermined curves corresponding to trajectories of spongy tissue of a natural implant site.

4. The process according to claim 1, wherein the step of forming the porous structural covering comprises providing a fabric selected from the group consisting of knitted, woven and braided fabrics.

5. The process according to claim 1, wherein the step of applying the covering to the base member comprises creating a change of the open-pore or open-cell structure as a function of location of the covering on the base member.

6. The process according to claim 1, wherein the implant is a femoral member of a hip joint endoprosthesis having a stem, and the step of applying the covering to the base member comprises disposing the covering on a proximal portion of the prosthesis stem in such a manner that the pores or cells are arranged along predetermined curves corresponding to trajectories of spongy tissue present in a natural implant site in a femur.

7. The process according to claim 6, wherein the step of applying the covering to the base member is carried out in such a manner that pore or cell size of the applied covering decreases toward a distal end of the prothesis stem.

8. The process according to claim 1, wherein the step of forming a porous structural covering comprises providing longitudinal webs crossed by traverse webs which intersect at predetermined angles corresponding to cutting angles of trajectories of spongy tissue of a natural implant site.

9. The process according to claim 8, wherein the step of forming a porous structural covering further comprises forming a hose of molding material from said webs, and the step of applying the covering to the base member comprises pulling the hose onto the base member.

10. The process according to claim 8, wherein the step of forming the porous structural covering further comprises constructing a hose of said webs, said hose having a constant diameter over its length, and the step of applying the covering to the base member comprises pulling the hose onto the base member.

11. The process according to claim 1, wherein the step of forming a porous structural covering comprises forming a hose of molding material, and the step of applying the covering to the base member comprises pulling the hose onto the base member.

12. The process according to claim 1, wherein the step of forming the porous structural covering comprises constructing a hose having a constant diameter over its length, and the step of applying the covering to the base member comprises pulling the hose onto the base member.

* * * * *